United States Patent
Bruins

(10) Patent No.: US 7,256,889 B2
(45) Date of Patent: Aug. 14, 2007

(54) MEASURING DEVICE, PARTICULARLY FOR CONDUCTING SPECTROSCOPIC MEASUREMENTS

(76) Inventor: Hans Joachim Bruins, Heerstrasse 7A, München (DE) 81247

( * ) Notice: Subject to any disclaimer, the term of this patent is extended or adjusted under 35 U.S.C. 154(b) by 324 days.

(21) Appl. No.: 10/511,950

(22) PCT Filed: Apr. 22, 2003

(86) PCT No.: PCT/EP03/04148

§ 371 (c)(1),
(2), (4) Date: Oct. 21, 2004

(87) PCT Pub. No.: WO03/089912

PCT Pub. Date: Oct. 30, 2003

(65) Prior Publication Data

US 2005/0213087 A1   Sep. 29, 2005

(30) Foreign Application Priority Data

Apr. 22, 2002 (DE) .................. 102 17 838
Apr. 25, 2002 (DE) .................. 102 18 485

(51) Int. Cl.
*G01J 3/28* (2006.01)
(52) U.S. Cl. .......... 356/326; 356/244; 356/246
(58) Field of Classification Search .......... 356/326, 356/244, 246
See application file for complete search history.

(56) References Cited

U.S. PATENT DOCUMENTS

| | | | |
|---|---|---|---|
| 4,168,294 A | 9/1979 | Calzi et al. | |
| 4,692,620 A | 9/1987 | Rosenthal | |
| 5,100,238 A | 3/1992 | Nailor et al. | |
| 5,241,178 A | 8/1993 | Shields | |
| 5,347,358 A * | 9/1994 | Nebe et al. | 356/246 |
| 5,568,262 A * | 10/1996 | LaChapelle et al. | 356/427 |
| 5,694,221 A | 12/1997 | Knapp | |
| 5,946,088 A * | 8/1999 | Aldridge | 356/300 |
| 6,249,344 B1 * | 6/2001 | Virag | 356/244 |
| 6,281,501 B1 | 8/2001 | Rosenthal et al. | |
| 2001/0000910 A1 | 5/2001 | Rosenthal et al. | |

FOREIGN PATENT DOCUMENTS

| | | |
|---|---|---|
| DE | 39 12 724 A1 | 11/1989 |
| JP | 11337485 A | 12/1999 |
| WO | WO 00/25110 A1 | 5/2000 |

* cited by examiner

Primary Examiner—Gregory J. Toatley, Jr.
Assistant Examiner—Kara Geisel
(74) Attorney, Agent, or Firm—Caesar, Rivise, Bernstein, Cohen & Pokotilow, Ltd.

(57) ABSTRACT

A measuring arrangement, in particular for spectroscopic measurements on particulate samples, is described, having a measuring cuvette (10) for sampling which has at least one window (11) through which the sample (3) can be irradiated and including a rotating mount (20) with which the measuring cuvette (10) can be rotated about a predetermined axis of rotation (1), whereby the alignment of the axis of rotation (1) deviates from a vertical reference direction.

14 Claims, 2 Drawing Sheets

MEASURING DEVICE, PARTICULARLY FOR CONDUCTING SPECTROSCOPIC MEASUREMENTS

BACKGROUND OF THE INVENTION

This invention relates to a measuring arrangement, in particular for performing optical spectroscopic measurements on particulate or liquid samples. The invention also relates to a measuring method for performing optical spectroscopy on particulate or liquid samples.

It is known from food technology that particulate samples (e.g., cereal grain, seeds or the like) may be subjected to optical spectroscopic measurements to obtain information regarding certain properties of samples, such as their chemical composition, water content, surface hardness, etc.

For example, reflection or transmission measurements may be performed with wavelengths in the visible or infrared spectral range. Conventional measuring arrangements for performing spectroscopy on cereal grain include a measuring cuvette for accommodating to the cereal grains and a spectrometer set up for highly sensitive transmission measurements, for example. The cuvette is exposed to light on one side. Light that passes through the cuvette due to surface reflections is detected on the opposite side. In contrast with conventional spectroscopy on liquids, the measurement results in spectroscopy on particulate samples show a sensitive dependence on the arrangement of the particles in the cuvette. Depending on the properties of the particles, such as volume, surface structure, etc., different packing densities may occur in a cuvette, thereby limiting the accuracy and reproducibility of the measurement results.

To overcome these problems, it has been proposed in the past that multiple measurements be performed on a measuring cuvette and that the measurement results be subjected to a statistical analysis. In practice, for example, it is known that the measuring cuvettes may be arranged on rotary tables that have been developed as sample holders for measurements on meat, yogurt or the like. A rotary table includes a shallow dish into which a sample of cereal grain is poured. For the spectroscopic measurement, different areas of the horizontally aligned dish are moved into the path of the beam of the spectrometer. This is accomplished by rotating the dish about a vertically aligned axis of rotation. The reproducibility of the measurement results has been improved by performing multiple measurements at different locations on a layer of particles. Nevertheless, corruption of the measurement results obtained with the horizontally adjustable rotary table has been found for the following reasons.

First, the layer in the dish does not have a uniform thickness and density. Heaps of particles are formed, causing variations in the distance from the illumination optics or the detector on the one hand and on the other hand causing the layer thickness to vary from one position to the next. In addition, certain bulk profiles develop when particles are poured in. Depending on the particle properties, the smaller or larger particles will be at the top of the dish. This results in separation and thus selection of the particles that contribute to the measurement. Finally, the available quantity of sample is frequently too small to fill a dish-like cuvette with a sufficient layer thickness. However, the extent to which the size of the cuvette can be reduced is limited because of the dimensions of the optical measurement beam and the individual particles.

Because of the low precision and reproducibility of the measurement results, spectroscopic measurements of grain have so far been of little value. For example, they are suitable for a rough classification of a grain quality, but not for a differentiated evaluation of varieties, for example, or for detecting contaminants or fusaria. There is a great deal of interest in particular in detecting even the smallest amount of impurities or fungi with a high reliability. Thus, in the case of a fusaria infestation, even if only one grain in 200 is found to have microtoxins on its surface, this is a finding which will prevent the use of this grain in a brewery. The infested cereal grain must be discovered among a multitude of grains. This presupposes in particular that the grain is positioned in the optical measurement zone so that microtoxins can be detected spectroscopically.

These problems occur not only in testing cereal grains or other agricultural products but also in general in characterizing particulate free-flowing samples or samples suspended in a liquid medium, in particular materials such as plastic granules, construction materials or the like.

The object of this invention is to provide an improved measuring arrangement, in particular for spectroscopic measurement of particulate or liquid samples with which the disadvantages of conventional measuring arrangements are overcome and which will be characterized in particular by an increased sensitivity, precision and reproducibility. Furthermore, the inventive measuring arrangement should have an expanded range of applications and should be suitable for measurement on a variety of particulate or liquid samples. The object of this invention is also to provide a method for spectroscopic measurement of particulate samples or liquid samples with which the disadvantages of the conventional methods are overcome. The improved method should permit in particular an increased sensitivity, precision and reproducibility of the measured value acquisition and should be compatible with essentially known spectroscopic measurement principles.

SUMMARY OF THE INVENTION

The basic idea of this invention is to provide a measuring arrangement with a measuring cuvette for accommodating a particulate or liquid sample and a rotating mount with which the measuring cuvette can be rotated about a predetermined axis of rotation, whereby the alignment of the axis of rotation deviates from the vertical direction (direction of gravitation). In contrast with the conventional technology with horizontal rotary tables with which all parts of a sample are in a mutual equilibrium of forces and therefore are immovable in relation to one another, the equilibrium of forces is disturbed due to the tilting of the axis of rotation out of the vertical direction according to this invention with each rotation of the measuring cuvette. For each rotation of the measuring cuvette, the equilibrium between the normal forces with respect to the surrounding particles (or a surrounding fluid) and gravitation is altered for each partial sample. Due to the rotation of the measuring cuvette into different measurement positions, there is continuous mixing of the sample. Advantageously, inhomogeneous bulk profiles, selective particle irradiation, varying bulk densities and the like are advantageously avoided or reliably compensated by statistical post-processing. In the case of liquid samples, there is also mixing, homogenization of the sample and/or an increase in the effective measurement area.

The measuring arrangement is advantageously suitable for various essentially known spectroscopic measurement methods, in particular for transmission or reflection measurements.

According to a preferred embodiment of this invention, the axis of rotation of the measuring cuvette is aligned horizontally, i.e., at a right angle to the vertical. In the case of a horizontal alignment, mixing of the sample with the adjustment of the measuring cuvette is especially great. In addition, there are advantages with respect to the adjustment of a respective spectrometer.

The measuring cuvette is preferably equipped with a coupling device with cooperates with a driving device for the rotational mount. Thus, the design of the measuring arrangement and in particular the insertion of the measuring cuvette into the rotating mount are simplified when an electric drive is provided for the measuring cuvette. The coupling device includes, for example, a coupling surface which extends at least partially over a cuvette edge and/or a groove for a belt drive. Special advantages occur in handling the measuring arrangement when the coupling surface is a friction surface and the rotational mount has a friction wheel as the driving device.

According to another advantageous embodiment of this invention, the measuring cuvette is formed by a structure of two shells held together by a ring frame. One of the shells may be charged with a sample, as is known with conventional measuring arrangements, and then sealed with the second shell. The composite is tightly sealed with the ring frame, which preferably has the coupling surface or groove on its outside. It is advantageous if the two shells have different volumes. By completely filling the larger shell, it is possible to ensure that more than half of the cuvette volume will be filled even in the tilted state. According to a modified embodiment, the measuring cuvette may have a lateral opening which advantageously facilitates charging and removal of samples.

The mixing effect of the measuring cuvette which is rotationally mounted and tilted is advantageously increased if mechanical mixing elements are mounted in the interior of the measuring cuvette to ensure an additional redistribution of the sample with rotation of the measuring cuvette.

An independent subject of the present invention is also a rotational mount for a measuring cuvette. The rotational mount forms a carrier with which a measuring cuvette is mounted so that it can rotate about an axis of rotation which differs from the vertical direction.

Another subject of this invention is a measuring device which is equipped with the inventive measuring arrangement and a spectrometer. It is of particular advantage that the measuring cuvette can be positioned without any special structural measures with the rotating mount in essentially known spectrometer arrangements. To this end, an actuating unit is provided, if necessary, which allows to move the measuring cuvette from a loading position, in which the measuring cuvette can be inserted into the rotating mount, into a calibration position and/or a measurement position in which a calibration and the actual spectroscopic measurement are performed.

Another subject of this invention is a method for spectroscopic measurement on particulate or liquid samples with which a sample is arranged in a measuring cuvette and a plurality of spectroscopic measurements is performed repeatedly, with the measuring cuvette being rotated between two measurements, this rotation being about an axis of rotation that deviates from the vertical direction. With each rotation of the cuvette, the sample is stirred or mixed so that each measurement is performed on a different amount of sample. After each revolution of the measuring cuvette, the parts of the sample in the path of the beam of the arrangement for spectroscopic measurement will have a different geometric distribution. The relative positions of the particles or the parts of a liquid sample are altered by each rotation. This advantageously permits an improvement in the statistical analysis of the measurement results.

The invention has the following additional advantages. First, the sample in the measuring cuvette has a defined layer thickness. In all measurement positions, the geometry of the measuring cuvette is constant in relation to the spectrometer, thereby further improving the reproducibility of the measurement. The layer thickness is adjustable, in particular with the shell design of the measuring cuvette described below, depending on the properties of the sample and the requirements of the measurement. The invention permits a statistical analysis of measurement results even with small quantities of sample. Due to the repeated rotation of the measuring cuvette with particulate samples, a wide variety of bulk materials can be adjusted even with a small number of particles, which supply statistically independent measurement results.

Another unexpected advantage is obtained with particulate samples from the sample bulk material in the cuvette. It has been found that when the cuvette is inclined, a narrower filling is made possible due to the rotation of the cuvette when it is set at an inclination than would be the case with horizontal shells filled in the conventional way. Fewer voids are formed. The probability of direct light passage through the measuring curve declines. This makes it possible to adjust a layer thickness that is even smaller.

This invention has a wide range of applications with various types of samples, such as agricultural products (cereal grain, grain products, vegetables, peas, soybeans, coffee beans, seeds, spices, rapeseed and the like), particulate materials with technical applications (e.g., plastic granules, construction materials, pigments) and the like and with various measurement functions, e.g., in detection of chemical or physical parameters of particles in the free bulk state or suspended in a liquid medium or (in the case of agricultural products) in detection of varieties, quality parameters, impurities, fungus infestation, genetic manipulation or the like.

BRIEF DESCRIPTION OF SEVERAL VIEWS OF THE DRAWINGS

Additional details and advantages of this invention are derived from the following description of the accompanying drawings, which show.

DETAILED DESCRIPTION OF PREFERRED EMBODIMENTS OF THE INVENTION

The invention is described on the example below with reference to a measuring arrangement for spectroscopic analysis of grain samples. However, implementation of the invention is not limited to the illustrated geometry of the measuring cuvette which is adapted to the analysis of grain, the design of the rotating mount, the arrangement of the spectrometer or the like.

Figure 1:
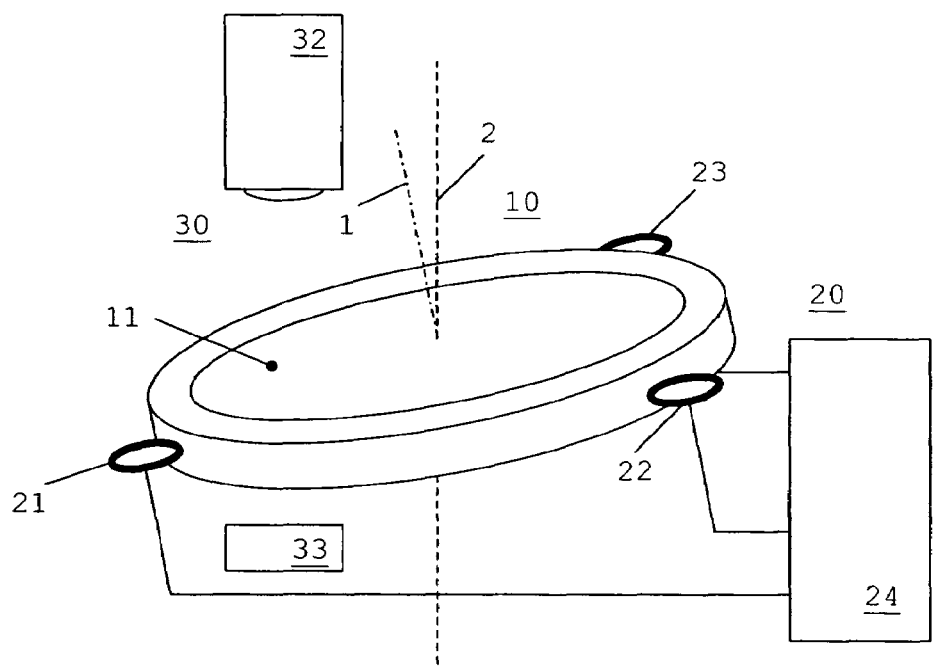
FIG. 1: a schematic illustration of a first embodiment of an inventive measuring arrangement.

FIG. 1 shows a measuring cuvette 10 and a rotating mount 20 as parts of an inventive measuring arrangement. The measuring cuvette 10, which is described in greater detail below, in general forms a container for the sample (not shown). The measuring cuvette has at least one window 11 which is formed by a transparent planar side wall, for example. For reflection measurements, it is sufficient to provide a window 11. For transmission measurements, two windows are provided, preferably formed by two transparent parallel side walls of the measuring cuvette 10.

The rotating mount 20 includes in general one or more carriers 21-23 with which the measuring cuvette 10 is rotatably mounted. The carriers 21-23 are designed so that the measuring cuvette (in particular the container which is formed by the measuring cuvette 10) can rotate about an axis of rotation 1 aligned fixedly in the space. According to the invention, the axis of rotation 1 is tilted by a predetermined angle with respect to a reference line 2, whereas the reference line 2 runs parallel to the vertical or the direction of gravitation (or acceleration of fall). The axis of rotation 1 is thus aligned such that a different total force comprised of bearing forces and gravitational forces acts on each particle in the measuring cuvette 10 in each rotational position. With each rotation of the cuvette, all or almost all of the particles move.

The angle between the axis of rotation 1 and the vertical reference line 2 can be selected depending on the application. In the case of a highly mobile or free-flowing bulk particle volume, tilting only slightly out of the vertical, e.g., by at least 5° is sufficient to induce the inventive mixing of the sample in the measuring cuvette with each rotation. Preferably, however, larger angles of at least 30° and in especially preferably the right angle (90°) are set (see FIG. 2).

The design of the carriers 21-23 is selected according to the geometry and the type of force transmission. In general, the mechanical components available in construction technology may be used as carriers for rotatable mounting and for the rotational drive of an object. For example, three mounting disks or mounting wheels are shown as carriers, these mounting wheels or mounting disks being mounted at an inclination in a stationary system and running, e.g., on the outside surface of the measuring cuvette 10 or in a groove formed therein. Preferably at least one of the carriers is designed as a driving device 23, e.g., as a friction wheel or a rubber roller (see FIG. 2). The mounting disks or mounting wheels may be replaced by ball bearings or pin bearings.

One or more of the carriers 21-23 is/are connected to a control device 24 with which the operation of the rotating mount 20 can be controlled. However, it is not absolutely necessary for the rotating mount 20 to be equipped with a driving device 23. As an alternative, a manual rotation of the measuring cuvette 10 may also be provided.

According to a preferred embodiment of the invention, the carriers 21, 22 and the driving device 23 form a self-tensing drive. During operation, the friction wheel 23 presses the cuvette against the carrier, which is adjacent in the direction of rotation. To do so, one of the carriers 21, 22 is arranged at an angle of 90°, for example, in relation to the friction wheel 23.

The inventive measuring device also contains a spectrometer 30 in addition to the components 10 and 20 already indicated. The spectrometer 30 is indicated schematically in FIG. 1 with the illumination optics 32 and a detector 33 for the transmission measurement. The illumination is provided with monochromatic light or polychromatic light (in particular white light). Depending on the type of spectroscopic measurement, other spectrometer geometries may also be provided as an alternative. The spectrometer 30 may be, for example, an integrating sphere (Ulbricht sphere) for reflection measurements. In addition, a monochromator may also be provided on the detector side of the sample. The measuring device is equipped with a housing (not shown) to screen out ambient light.

An inventive measuring cuvette 10 is advantageously equipped with a coupling device which cooperates with the driving device of the rotational mount. Depending on the drive principle, the coupling device may be, for example, a coupling surface such as a toothed surface or a friction surface or it may have a groove for accommodating a belt drive. In addition, mechanical components such as levers or the like may be provided on the edge of the measuring cuvette.

Figure 2:
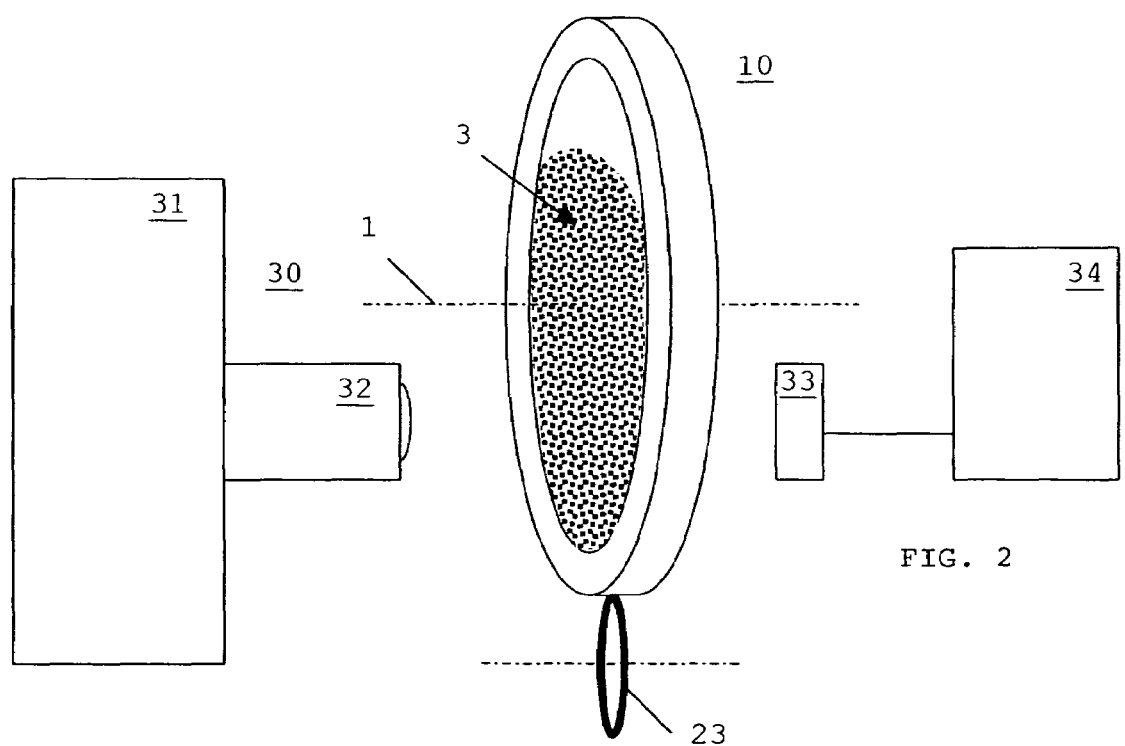
FIG. 2: a schematic illustration of another embodiment of an inventive measuring arrangement.

A modified design of the inventive measuring device is illustrated in a detail in FIG. 2. In this embodiment, the measuring cuvette 10 is arranged with a horizontal axis of rotation. Of the rotating mount 20, only the driving device which is designed as a friction wheel 23 is shown here. The spectrometer 30 includes a light source 31 (e.g., a white light source with a monochromator or a tunable laser light source), a lighting optics 32, a detector 33 and an analyzer device 34. The measuring path from the lighting optics 32 to the detector 33 is arranged horizontally like the axis of rotation of the measuring cuvette 10. The spectrometer 30 may contain other optical components which are essentially for conventional spectrometers, e.g., a filter wheel or an interference filter. The parallel alignment of the optical measurement path and the axis of rotation is not an obligatory feature of the invention but is preferred according to the invention for easy adjustment.

An inventive measuring method for spectroscopic analysis of grain has the following sequence, for example. First the sample 3 (consisting of a plurality of particles, e.g., cereal grains) is placed in the measuring cuvette. Depending on the design, this is done through an opening provided for this purpose or by assembling a cell structure (see FIGS. 4 and 5). The sample 3 preferably fills more than 50% of the cell volume but not the total volume. The filling level is selected depending on the material for measurement and is adjusted so that in the measurement position approximately 30% of the window 11 remains free. In this way the mobility of the sample in the measuring cuvette is ensured and a calibration measurement is made possible.

After filling the measuring cuvette 10 it is placed in the rotating mount. Depending on the measurement task, a calibration may have to be performed first. The measuring cuvette 10 is therefore placed in the optical measurement path in such a way that the measurement light passes through the measuring cuvette and reaches the detector 33 without any interaction with the sample 3. After calibration, the measuring cuvette 10 is placed in a first measurement position. In this measurement position, the sample 3 is positioned in the optical measurement path. A spectroscopic measurement is performed on the sample 3. The implementation of the invention is not limited to certain spectroscopic measurement methods for detecting the interaction of visible or infrared light with the sample. In particular reflection, transmission or fluorescence measurements or measurement methods derived therefrom e.g., time-resolved methods, nonlinear methods) may also be provided.

For example, a transmission measurement is performed. For a quantitative analysis (so-called chemometrics) of cereal grain, a sample is illuminated with a wavelength in the range of 740 nm to 1100 nm, for example. In the case of a sample layer thickness in the measuring cuvette 10, the optical density is approximately 4. The transmission measurement includes essentially a known run through the wavelength range that is of interest and a detection of the light passed by the sample. Depending on the measurement task, different wavelength ranges, in particular in the visible range, may also be set. This is also true of reflection measurements in which the measurement wavelength or the wavelength range is selected as a function of the sample investigated in particular.

After a first measurement in the first measurement position, the measuring cuvette 10 is rotated. It is rotated about the axis of rotation 1 by a certain angle of rotation. The angle of rotation is selected according to the mobility of the sample and the mechanical design. In the case of grain, for example, a rotation by 30° is used. In the new measurement position, another transmission measurement is performed. The spectroscopic measurement is preferably generally performed on a stationary measuring cuvette 10. However, basically measurement tasks in which the measuring cuvette 10 is rotated continuously during the measurement are essentially also possible. After the transmission spectra or individual transmission values have been recorded in the different measurement positions, a statistical analysis is performed according to known methods.

Measurements on grain have shown that transmission measurements on 16 measurement positions, i.e., after 16 rotations, yield excellent results. When there are 50 measurements the standard deviation is less than 0.02 which is better by a factor of 4 than the results with conventional analyzers.

As an alternative, the sample 3 may comprise particles in a state in which they comprise a liquid or are suspended in a liquid (liquid solution, etc.). The particle arrangement (or liquid) is inverted with each revolution and/or any particles that have sedimented in the meantime are redistributed. Suspension samples include, for example, suspended pigment particles, emulsions with added particles (e.g., milk, oils with solids and the like). The viscosity and layer thickness can be selected according to the measurement task and the sample may also be in the form of a suspension or paste having a low fluidity.

Figure 3:
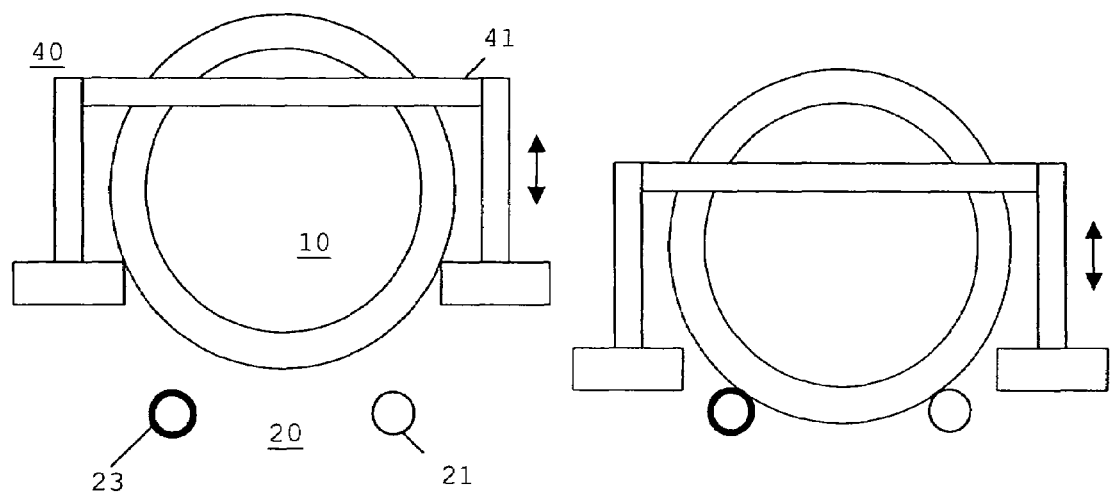
FIG. 3: illustrations of the function of an actuator unit for handling a measuring cuvette according to the invention.

For manipulation of the measuring cuvette 10, preferably an actuator unit 40 is used (diagrammed schematically in FIG. 3). The actuator unit 40 includes a movable mounting frame 41 with which the measuring cuvette 10 can be moved from a loading position (left part of FIG. 3) into a measurement or calibration position (right part of FIG. 3). In the loading position, the measuring cuvette 10 is lifted up from the rotational mount. The measuring cuvette 10 may easily be inserted manually into the holding frame 41 or removed from it. By lowering the holding frame 41 vertically onto the rotating mount, of which only a carrier 21 and a friction wheel 23 are illustrated, the measuring cuvette 10 is placed in the operating state. The mechanical drive (not shown) with which the holding frame 41 is operated may at the same time also be used for moving the rotating mount in the vertical direction for the change between the calibration position and the measurement position.

Figure 4:
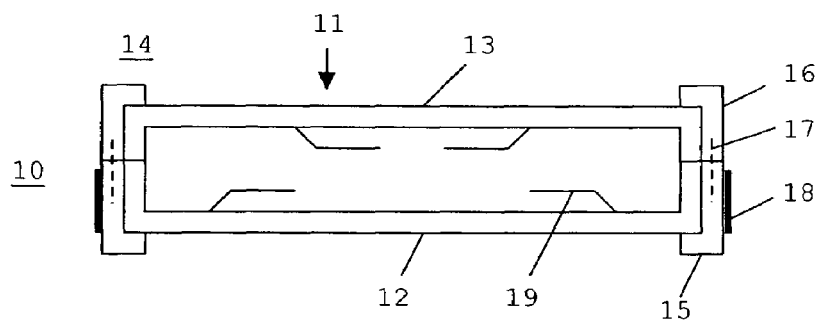
FIG. 4: a schematic sectional view of a preferred embodiment of an inventive measuring cuvette.
Figure 5:
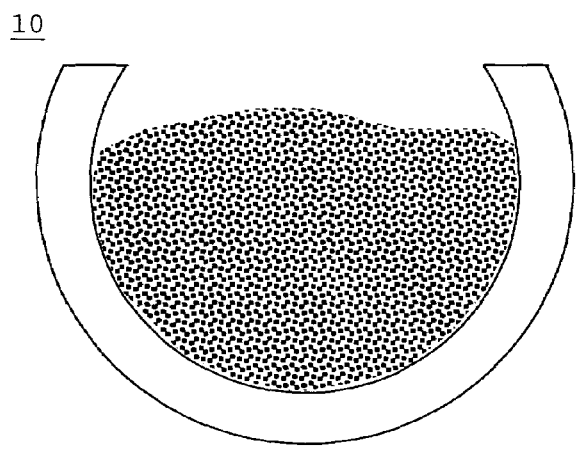
FIG. 5: a side view of another embodiment of an inventive measuring cuvette.

FIGS. 4 and 5 show two embodiments of can-shaped measuring cuvettes 10 with which the invention is preferably implemented and which themselves constitute an independent object of this invention. According to FIG. 4, a measuring cuvette includes a lower shell and an upper shell 12, 13, each having a planar bottom (forming the cuvette window) and a peripheral edge and they are held together by a ring frame 14 with the edges held in contact. For performing measurements on liquid samples the edges are equipped with gaskets. The ring frame 14 consists of a lower ring 15 and an upper ring 16. The rings 15, 16 may be aligned in relation to one another by holding pins 17 and held together with permanent magnets which are integrated into the rings. The reference number 18 refers to a friction surface which is provided peripherally on the outside of the lower ring 15.

In the interior of the shells 12, 13, mixing elements 19 are provided. The mixing elements 19 include, for example, levers, hooks, steps or the like. They are arranged so that they do not interfere with the optical beam path in the measurement position. The mixing elements 19 have special advantages in mixing suspended particles or solutions.

The shells 12, 13 form the windows of the measuring cuvette 10. In general, the windows are planar transparent side walls. For example, they may be made of glass (e.g., BK270 glass with a thickness of 1 mm) or a plastic having suitable optical properties. The measuring cuvette 10 is preferably aligned with the rotating mount 20, so that the axis of rotation 1 (see FIG. 1) is perpendicular to the plane of the window (or the bottom of the shell).

In the example illustrated here, the measuring cuvette 10 has a diameter of approximately 10 cm, for example. In the interior of the cuvette, a layer thickness which is selected as a function of the measuring object in particular is selected. For example, it amounts to approx 5 mm for measurements on rapeseed, approximately 8 mm to 18 mm for measurements on cereal grain and approximately 30 mm for measurements on corn. However, these are only examples. Smaller layer thicknesses are also possible, e.g., for performing measurements on spices or suspensions, and larger layer thicknesses are also possible.

The fact that the measuring cuvette is composed of partial shells has the advantage of rapid charging, easy cleaning and flexible adaptation of the measuring layer thickness to the particular sample. The two shells 12, 13 preferably have different volumes. The sample is added to the larger shell. The filling level in the tilted measuring cuvette then corresponds to the volume ratio of the two shells, i.e., 1/3:2/3, for example.

As an alternative, the measuring cuvette 10 may be opened on one side according to FIG. 5. In this design, there is slewing motion with the rotating mount with an occasional, e.g., alternately reversing the direction of rotation. Charging of the sample is simplified with the cuvette opening.

The features of this invention disclosed in the preceding description, drawings and claims may be may be important individually and in any combination for implementation of this invention in the embodiments.

What is claimed is:

1. A measuring arrangement for spectroscopic measurements on a particulate or a liquid sample, said measuring arrangement comprising:

a measuring cuvette for accommodating the sample, having at least one window through which the sample can be exposed to radiation, and comprising two shells adapted to form a container for the sample when assembled together;

a rotating mount with which the measuring cuvette can be rotated about a predetermined axis of rotation, wherein an alignment of the axis of rotation deviates from a vertical reference direction; and an actuator unit with which the measuring cuvette can be moved from a loading position into a calibration position or a measurement position.

2. The measuring arrangement according to claim 1, wherein the axis of rotation is aligned horizontally.

3. The measuring arrangement according to claim 1, wherein the measuring cuvette has a coupling device which cooperates with a driving device of the rotating mount.

4. The measuring arrangement according to claim 3, wherein the coupling device has a coupling surface or a groove for a belt drive.

5. The measuring arrangement according to claim 1, wherein the two shells are held together by a ring frame.

6. The measuring arrangement according to claim 5, wherein the two shells have different volumes.

7. The measuring arrangement according to claim 1, wherein the measuring cuvette contains mechanical mixing elements.

8. The measuring arrangement according to claim 1, wherein the measuring cuvette has an opening for sample charging and removal.

9. The measuring arrangement according to claim 1, further comprising a spectrometer which is optically coupled to the at least one window.

10. A method for spectroscopic measurement of a particulate or liquid sample, said method comprising the steps of:

providing a measuring arrangement according to claim 1, arranging the sample in the measuring cuvette, and performing at least two spectroscopic measurements, wherein between the measurements, the measuring cuvette is rotated about the predetermined axis of rotation.

11. The method according to claim 10, wherein the measuring cuvette is rotated about a horizontal axis of rotation between two measurements.

12. The method of claim 10, comprising the step of spectroscopic analysis of particulate, free-flowing or suspended or liquid samples.

13. The method according to claim 12, wherein said samples comprise agricultural products.

14. The method according to claim 13, wherein said agricultural products comprise cereal grain or suspensions.

* * * * *